(12) United States Patent
Maleeny et al.

(10) Patent No.: US 7,135,169 B2
(45) Date of Patent: Nov. 14, 2006

(54) AIR SCENTING COMPOSITIONS FOR SPRAY APPLICATION ON AIR SCENTING DEVICES

(75) Inventors: Robert Maleeny, Ramsey, NJ (US); Kevin Vick, Thomasville, GA (US); James Kinney, Ramsey, NJ (US); David Ziser, Pompton Plains, NJ (US); Richard Laky, Clifton, NJ (US)

(73) Assignee: Scentco, LLC, Thomasville, GA (US)

( * ) Notice: Subject to any disclaimer, the term of this patent is extended or adjusted under 35 U.S.C. 154(b) by 560 days.

(21) Appl. No.: 10/278,669

(22) Filed: Oct. 23, 2002

(65) Prior Publication Data

US 2004/0082495 A1   Apr. 29, 2004

(51) Int. Cl.
  A61L 9/00    (2006.01)
  A61L 9/14    (2006.01)
  A61L 9/04    (2006.01)
  A61K 8/00    (2006.01)

(52) U.S. Cl. .................. 424/76.1; 424/76.2; 424/76.21; 424/76.4; 424/43; 424/45; 424/47

(58) Field of Classification Search .................. 424/43, 424/45, 47, 76.1, 76.2, 76.21, 76.4, 3; 222/3
See application file for complete search history.

(56) References Cited

U.S. PATENT DOCUMENTS

| | | |
|---|---|---|
| 2,871,526 A | 2/1959 | Bulloff |
| 3,994,439 A | 11/1976 | Van Breen et al. |
| 4,065,262 A | 12/1977 | Petroff |
| 4,095,031 A | 6/1978 | Engle |
| 4,102,656 A | 7/1978 | Koritz |
| 4,118,226 A | 10/1978 | Bourass |
| 4,159,672 A | 7/1979 | Garguilo et al. |
| 4,257,787 A | 3/1981 | Taylor |
| 4,523,870 A | 6/1985 | Spector |
| 4,563,333 A | 1/1986 | Frigon |
| 4,587,129 A | 5/1986 | Kliment |
| 4,603,030 A | 7/1986 | McCarthy |
| 4,604,114 A | 8/1986 | Ward |
| 4,735,358 A | 4/1988 | Morita et al. |
| 4,903,583 A | 2/1990 | Frazier |
| 4,938,416 A * | 7/1990 | Bertrand et al. |
| 4,959,087 A | 9/1990 | Kappernaros |
| 4,988,744 A | 1/1991 | Yamamoto |
| 5,034,222 A | 7/1991 | Kellett et al. |
| 5,063,256 A | 11/1991 | Hoshino et al. |
| 5,078,046 A | 1/1992 | Mascolo et al. |
| 5,087,273 A | 2/1992 | Ward |
| 5,240,653 A | 8/1993 | Ramkissoon |
| 5,273,690 A | 12/1993 | McDowell |
| 5,297,988 A | 3/1994 | Nishino et al. |
| 5,324,490 A | 6/1994 | Van Vlahakis et al. |
| 5,417,929 A | 5/1995 | Kita |
| 5,547,636 A | 8/1996 | Vick et al. |
| 5,698,166 A | 12/1997 | Vick et al. |
| 6,087,310 A * | 7/2000 | Henkel |
| 6,117,218 A | 9/2000 | Snyder et al. |

(Continued)

Primary Examiner—Humera N. Sheikh
(74) Attorney, Agent, or Firm—Welsh & Katz, Ltd.

(57) ABSTRACT

Aqueous compositions as well as processes and devices are disclosed for spray application on an air scenting device to provide long lasting freshening or scenting of air flowing through the device with minimal blockage of air flow through the device. The compositions contain a polymeric emulsion, a surfactant and a fragrance material and also may optionally include a rheological agent and/or an anti-microbial agent.

10 Claims, 2 Drawing Sheets

U.S. PATENT DOCUMENTS

| | | |
|---|---|---|
| 6,238,646 B1 * | 5/2001 | Zembrodt |
| 6,325,475 B1 | 12/2001 | Hayes et al. |
| 6,339,897 B1 | 1/2002 | Hayes et al. |
| 6,379,242 B1 | 4/2002 | Wiseman et al. |
| 6,390,453 B1 | 5/2002 | Frederickson et al. |
| 6,454,876 B1 * | 9/2002 | Ochomogo et al. |
| 6,479,456 B1 | 11/2002 | Holzner |
| 2001/0035095 A1 | 11/2001 | Canfield |

* cited by examiner

AIR SCENTING COMPOSITIONS FOR SPRAY APPLICATION ON AIR SCENTING DEVICES

BACKGROUND OF THE INVENTION

1. Field of the Invention

The present invention relates generally to scenting compositions formulated for spray application on air scenting devices and to the devices having such scented compositions applied thereon as well as to processes for application of the scenting compositions to air scenting devices. More particularly, it relates to scented or fragranced compositions for spray application on devices such as air filters, for example, in mechanical forced air heating, ventilating and air conditioning ("HVAC") systems to provide long lasting freshening or scenting of air flowing through the devices with minimal blockage of air permeating therethrough.

2. Description of Related Art

The use of air scenting or freshening devices has long been known for use in releasing fragrances of various types in ambient air. Such devices have been used successfully for purposes of scenting and/or freshening air in confined spaces, particularly to mask odors such as may occur in the form of cooking odors, pet odors, tobacco smoke and the like. Furthermore, such devices have been adapted for use in mechanical HVAC systems wherein air is circulated within an interior space.

The general concept of providing a sustained release mechanism for air freshening the home is the subject of numerous patents and consumer products. Leading commercially available products in this category have common design elements which include 1) a sponge like/cardboard substrate which is mounted to the filter, 2) a fragranced gel/wax mixture which is coated/beaded onto the sponge or cardboard, 3) a plastic/metal mount which fixes the sponge or cardboard to the filter, 4) a foil wrap/packette outer package for insuring that the product will not loose fragrance after manufacturing and prior to purchase by the ultimate consumer.

These prior art air scenting/freshening devices, systems and compositions are described in the following exemplary U.S. Patents. For example, U.S. Pat. No. 2,871,526 describes an air odor control system including an odor control composition positioned in a porous container for dispensing vapors to control odors. U.S. Pat. No. 4,065,262 describes an air freshening apparatus utilizing an air filter element having a plurality of containers positioned in the air filter for holding an air freshening composition. U.S. Pat. No. 4,102,656 describes an odor conditioning apparatus including a filter element positioned to be dipped into a reservoir containing a liquid which will wick into the filter to be vaporized into the environment.

U.S. Pat. No. 4,118,226 describes an air freshening device wherein a solid aromatic medium is positioned in a perforated case which, in turn, is placed in a ventilating system. U.S. Pat. No. 4,604,114 similarly describes placing large solid rods of fragrant scented material in an air circulation system. Additionally, U.S. Pat. No. 4,563,333 describes a deodorizing fitting for an air filter in which a rectangular envelope of perforated cardboard with a deodorizing insert therein is adhered to a corner of the filter; U.S. Pat. No. 4,523,870 describes an aroma dispensing cartridge placed in front of an air vent and U.S. Pat. No. 4,735,358 describes a system wherein fragrant material is placed on a tape from which the material vaporizes when the tape is run across a tape head by drive means.

It should be noted that many of the above described prior art devices disadvantageously interfere with the normal flow of air through the HVAC system and cause blockage of air flow through air filters to which they are attached of about 10% or more of the total air engaging or impinging on the filter. Further, none of the aforesaid devices can be readily employed in a pre-existing filter systems. Rather, specifically designed frames or casings must be used to hold the fragrant structures.

In recent times a scented air freshening device has been developed which offers improved convenience and reduced air flow restriction when used with a standard air filter of a type found in conventional force air ventilation systems. This device is described in U.S. Pat. Nos. 5,547,636 and 5,698,166. As shown therein, a conventional air filter of the type including a porous mesh supported in a paperboard frame is fitted on its front or outwardly facing surface (i.e., the upstream surface of the filter which, when installed, faces the fan or other source of air flow in an HVAC system) with a portion of a flat porous substrate, such as an air permeable sponge material. The substrate is provided with a solution of fragrant material which may include a polymer and volatile solvent. When installed in an HVAC system, the solvent is allowed to evaporate leaving a dried fragrant polymeric residue on the substrate from which a fragrant scent is slowly released. Conveniently, the substrate may be attached to the front or outward facing surface of the air filter by the use of a simple barbed connector which pierces both the substrate and filter medium and holds the substrate in place. This device has proved to be most advantageous to homeowners who wish to use their HVAC systems to introduce and circulate a desirable fragrance throughout their homes. The device is essentially usable with any conventional furnace air filter and is highly cost effective in manufacture and sale.

Other generally similar air scenting/freshening devices adapted for installation on the front or outward facing surface of a conventional air filter in an HVAC system are described in U.S. Pat. No. 5,087,273 wherein the device comprises an air permeable envelope containing aromatic beads which is positioned on the upstream or air flow facing side of the filter to provide a fragrant scent to the air circulated through the system and in U.S. Pat. No. 6,117,218 wherein the device comprises a scenting device for attachment to the upstream face of an air filter comprising a sheet formed from a material which is substantially impervious to air having a viscous liquid, such as a gel, containing a fragrance applied thereto and including openings therein through which scented air flows into and through the filter. However, each of these devices suffers from the same problems as noted above relative to the devices described in U.S. Pat. Nos. 5,547,636 and 5,698,166.

Although the above-described substrate devices have provided certain improvements over the prior art, they are not without disadvantages. Primarily, in order to use the devices effectively, the substrates must be attached to the upstream front or outward facing surface of a ventilating system air filter. Attachment of these prior art substrates to the upstream surface of the filter has been necessary in order to eliminate the risk that would be presented if the substrate were to be affixed to the downstream surface of the filter. That is, if these substrates were positioned on the downstream surface, the substrate itself or disintegrated portions of the substrate could become dislodged from the downstream surface and could cause damage to the mechanical components of the HVAC system during operation. Also, the dislodged material can be directly disseminated into the environment with the HVAC air flow exiting from the filter on the downstream side thereof over extended periods of time of use.

However, when the substrates of the prior art are attached to the outward facing surface of the air filter to avoid this possible contamination problem, the substrates are naturally exposed to unfiltered particulate matter entrained in the ambient air entering the filter which has a tendency to cause premature blockage or clogging of the substrate and to, thereby, diminish its effectiveness of the device from releasing scented fragrance through the filter over time.

In our co-pending U.S. patent application Ser. No. 09/994,231, a further improved air freshening system is disclosed employing an air freshening composition comprising a thermoplastic, semi-permeable polymeric gel having a fragrance material incorporated therein. The composition is formulated for application to an air filter such as employed in an HVAC system to provide an air freshening scent to air passing through the filter by dispersing scented, volatile components into the air over a predetermined period of time. These gel composition have been found to be advantageous in overcoming many of the problems encountered with the prior art the substrates which must be attached to the upstream front or outward facing surface of a ventilating system filter. However, it has been recognized that the provision of a suitable spray on scenting composition that would provide long lasting air freshening or scenting to air passing through the filter without causing significant blockage of the filter surface would be extremely beneficial and could provide an even better and more cost efficient solution to the problems presented by the prior art.

In this regard, U.S. Pat. No. 4,159,672 describes apparatus for automatically introducing a scent into a forced air temperature changing system by pumping a scent containing fluid through tubes positioned adjacent to an air filter and spraying the pumped fluid onto the filter so that air flowing through the filter picks up the scent and brings the scent to the desired area. However, this patent provides no description of the formulation of the scent containing fluid nor does it provide any solution to the air flow blockage problem that would be presented by spraying such compositions onto a filter from the tubes. Still further, this patent does not suggest or teach the formulation of the scent containing fluid so as to provide long lasting freshening or scenting of air flowing through the filter.

Providing long lasting freshening or scenting or air in an HVAC system has been a continuing problem with prior art air freshening or scenting devices arising from the volatile nature of liquid fragrances. Fragrances for scenting air typically are liquid oils. Such fragrant oils are mixtures of many different chemicals. Most of the chemicals mixed into a fragrance oil are liquids, but some components are solid. A solvent is used to dissolve the components together to form a homogenous fragrant liquid oil. The components have relatively high vapor pressures. Thus, the fragrant liquids evaporate readily giving rise to fragrance "flash-off" problems during the manufacture of the devices. Fragrant liquid oils, therefore, are not satisfactory for use in forced air ventilation systems carrying air at significant velocities. The present invention accordingly, addresses the conflicting problems associated with the deodorizing and scenting of air in forced air ventilation systems of entraining an effective amount of scent into the air while achieving sufficient longevity of scenting activity.

Accordingly, there exists a continuing need for a scented air freshening composition which may be used in a HVAC heating, ventilating, and cooling system for deodorizing and freshening air distributed in the system and will cause minimal interference with the circulation of air through the system while providing sufficient scenting of the circulating air for a relatively extended predetermined period of time.

In view of the foregoing, it is a general object of the present invention to further improve over the prior art by providing a scented or fragranced composition for spray application on air filters used in air scenting devices and to devices and processes for scenting air circulated in an HVAC system or the like utilizing such spray applied scented or fragranced compositions.

Another object is to provide compositions for spray application on air filters used in a device and process for freshening or scenting air in an HVAC system or the like wherein the sprayed composition provides an air permeable coating layer on the surface of the air filter with the sprayed coating layer containing a volatile component which will evaporate over a relatively extended predetermined period of time to impart a desired fragrance to the surrounding environment.

A further object is to provide a device for freshening or scenting air in an HVAC system wherein a fragrant coating layer is sprayed onto a filter surface to freshen or scent the air and wherein the coating layer will not cause the filter to become blocked by particulate matter contained within ambient circulated air over a relatively extended period of time.

A still further object is to provide a composition for freshening or scenting air which is usable in a standard or conventional ventilating system air filter device and can conveniently be applied by spraying either on the front or outward facing surface of the air filter or, more preferably, on the reverse or inward facing surface of the filter so that only filtered air will impinge thereon.

Yet another object is to provide a device for scenting or freshening air which is convenient for application and which is highly cost-effective and efficient in use.

These and other objects will become apparent hereinafter to those skilled in the art.

SUMMARY OF THE INVENTION

We have found that the above stated objects as well as further improvements over the prior art may be achieved by providing specially formulated scenting compositions for spray application on air scenting devices such as air filters used in HVAC systems, central air conditioners, window air conditioners, automobile ventilation systems and the like to provide long lasting scenting of air passing through the devices with minimal blockage of air flow as well as the spray treated devices themselves and processes for spray application of the compositions on the devices.

Thus, in one embodiment, the present invention is directed to a scenting composition formulated for spray application on an air scenting device such as an air filter to provide a pleasant and long-lasting fragrance or aroma in an ambient surrounding, the scenting composition comprising an aqueous combination of a polymeric emulsion, a surfactant and a fragrance material.

In another embodiment, the present invention is directed to an air scenting device such as an air filter having an aqueous scenting composition sprayed thereon to provide long lasting freshening or scenting of air flowing through the device with the spray applied scenting composition causing minimal blockage of air flow through the device wherein the scenting composition comprises a polymeric emulsion, a surfactant and a fragrance material.

In a further embodiment, the present invention provides a process for producing an air scenting device which provides long lasting freshening or scenting of air flowing through the device wherein the process comprises spraying an aqueous scenting composition on the air scenting device in a manner such that the scenting composition causes minimal blockage of air flow through the device and the aqueous scenting composition comprising a mixture including a polymeric emulsion, a surfactant and a fragrance material.

In a still further embodiment of this invention, an aqueous scenting composition is employed which includes an antimicrobial agent or preservative to prevent microbial growth in and on the air filter having such composition sprayed thereon and/or to inhibit mold, mildew and like conditions from forming in and on the filter surface.

Accordingly, the present invention offers a number of significant advantages over the prior art. For example, we have discovered that the spray-on compositions of this invention offer a consumer friendly means for complete home air freshening with high levels of immediate and longer range fragrancing efficacies without impeding air flow through or furnace/air conditioning efficiency of filters on which the compositions are sprayed.

In formulating the spray-on compositions of this invention, latex polymer emulsions formed from polymeric substances such as styrene butadiene, acrylic, vinyl acrylic, styrene acrylic type latex polymers and the like are prepared having their chemistries balanced to accept high levels of fragrance, preferably in a range of about 1–50% by weight of the composition, and the compositions are water based to provide quick drying and flame retardation properties. Surfactant systems are included in the emulsions to provide excellent wetting characteristics when the compositions are sprayed on fibers such as fiberglass fibers of a scenting device such as an air filter.

Furthermore, we have found that rheology control additives such as gums, clays, cellulosics, dextrins, algins, polymeric thickeners and the like and mixtures thereof, optionally, also may be added to the latex polymer emulsion compositions of this invention in an amount sufficient to provide thixotropic, non-dripping characteristics after the compositions are applied on filters. The inclusion of the optional rheological additives in the formulations also enables the resulting compositions to crosslink and/or laminate during drying after application on a scenting device such as a filter to form a clear film for regulating a sustained release of fragrance components during extended time periods. Preferably, these optional rheological agents are incorporated in the compositions of this invention at a level of about 0.1 to about 20% (by weight of the composition).

Still further, bactericidal agents also may optionally be incorporated in the present compositions in an amount sufficient to prevent microbial growth and/or to inhibit mold and mildew growth and other bacterial growth on and in a filter treated with the scenting composition. Preferably, these optional bactericidal agents are incorporated in the compositions of this invention at a level of about 0.05% to about 1.0% (by weight of the composition).

In a preferred embodiment of this invention, the aqueous scenting compositions contain a latex polymer emulsion at a level of about 1.0 to about 50% (by weight of the composition), most preferably, at a level of about 25.0 to about 35% (by weight of the composition); a surfactant film forming agent at a level of about 0.1 to about 5% (by weight of the composition), most preferably, at a level of about 0.25 to about 1.0% (by weight of the composition); a fragrance material/fragrance oil at a level of about 1.0 and about 95% (by weight of the composition) and, most preferably, at levels between about 10 and about 50% (by weight of the composition) and water at a level of about 10 to about 60% (by weight of the composition), most preferably, at a level of about 25 to about 40% (by weight of the composition).

We have found that the present invention provides further improvements over the prior art by providing scenting devices formed by spraying or otherwise depositing aqueous scenting compositions onto an element within an HVAC system, preferably an air filter, so as to impart an air freshening scent or fragrance to air circulating in the system over an extended period of time. Preferably, the aqueous scenting composition is applied to a single face of an air filter at several distinct locations about the surface thereof although the composition may be applied at multiple positions on both the upstream and downstream faces of the filter simultaneously or as a single entity on either the upstream or the downstream face or both faces of the filter.

Additionally, the scenting composition may be applied to a filter in any selected pattern provided that the aqueous composition will not cause blockage of air flow through the filter of greater than about 0.1% of the total air engaging or impinging on the filter while the system employing such filter is in operation.

BRIEF DESCRIPTION OF THE DRAWINGS

The foregoing and other novel features and advantages of the invention will be better understood upon a reading of the following detailed description taken in conjunction with the accompanying drawing wherein.

DETAILED DESCRIPTION OF A PREFERRED EMBODIMENT OF THE INVENTION

Figure 1:
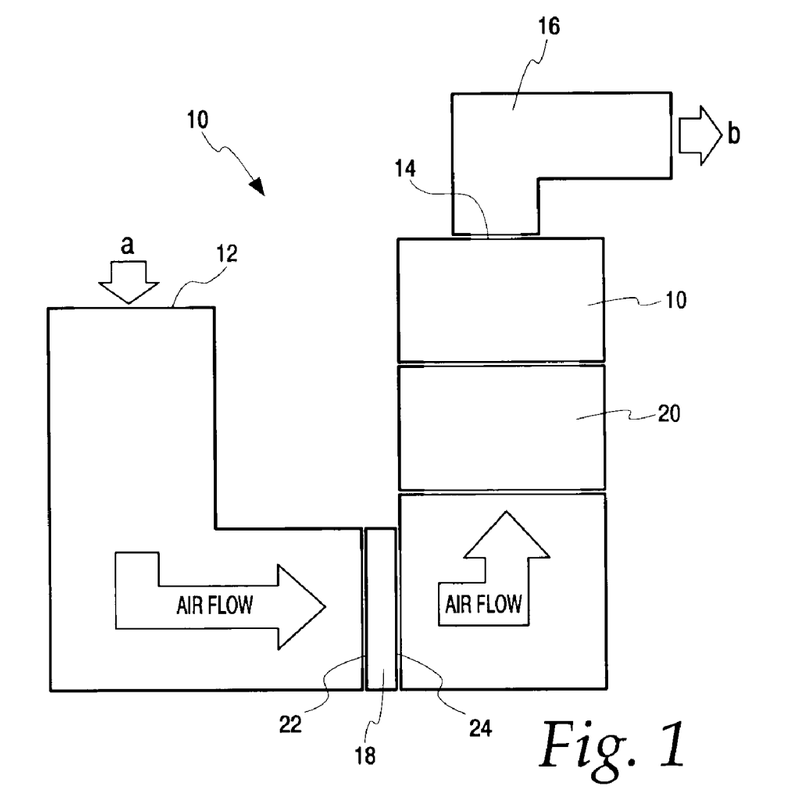
FIG. 1 is a schematic view of a standard forced air HVAC system.

We have unexpectedly discovered that certain fragrance systems can be incorporated into polymer emulsions and can then be used to create fragranced polymer films on various substrates such as air filters. Further, we have determined that after applying these special fragranced polymer emulsions to various substrates, the systems quickly form a polymer film at the emulsion/air interface. Once formed this film acts as a barrier which slows the rate of water evaporation and, therefore, film formation within the liquid. When considering the above as a means for extended time release of the fragrance components, many consumer products are possible.

Referring now to the drawings, FIG. 1 illustrates a conventional forced air heating, ventilating and air conditioning (“HVAC”) system wherein an HVAC housing indicated generally by the reference numeral 10 has an ambient air inlet end 12 and an outlet end 14 connected to an air outlet ducting 16 which disperses filtered air into the surrounding environment. Mounted in the housing 10 is a filter 18 and a fan or blower assembly 20 for controlling the ambient air flow through the housing 10 in the direction indicated by arrows a and b from the inlet end 12 of the housing through the filter 18 from the filter's upstream facing surface 22 to its downstream facing surface 24 and then to outlet end 14 of the housing 10 and into the air outlet ducting 16 for distribution into the surrounding environment.

Figure 2:
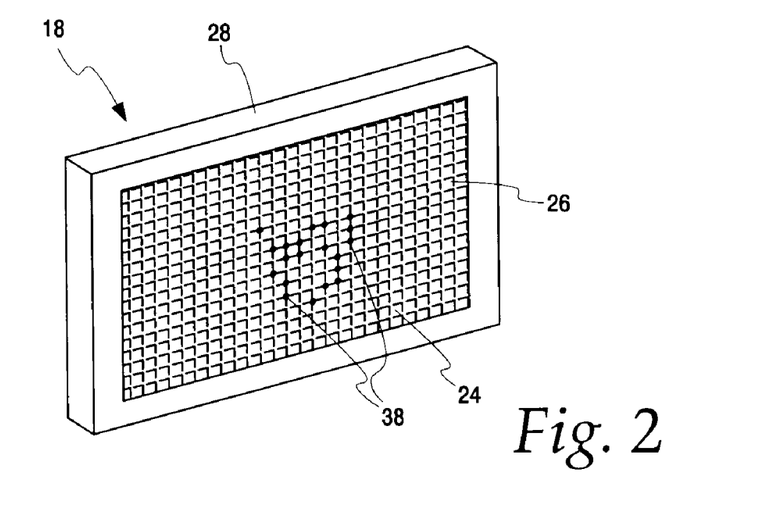
FIG. 2 is an enlarged isometric view of an air filter used in the forced air HVAC system of FIG. 1 having a novel aqueous scenting composition applied to an air permeable surface thereof.

FIG. 2 shows a heretofore standard air filter 18 of a commercially available type typically provided for use in an HVAC system such as that depicted in FIG. 1. The filter 18 in conventional form is comprised of a fibrous air permeable filter medium 26, such as a textile material, fiberglass or other woven fibers that arrest particles in the interstices of the medium 26. Typically a suitable rigid or semi-rigid frame 28 surrounds the periphery of the filter medium 26 for holding the medium 26 in position.

Figure 3:
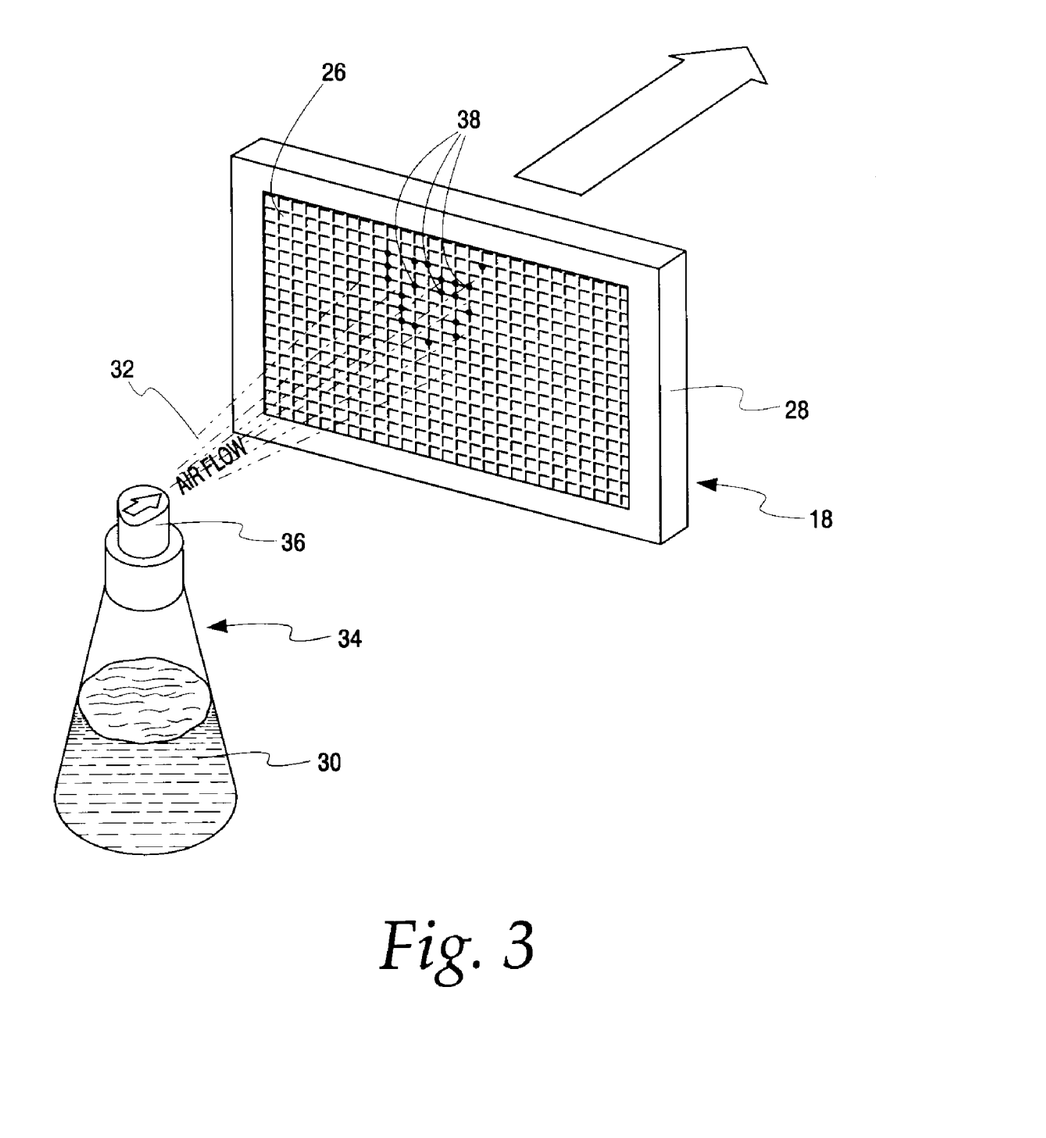
FIG. 3 is a perspective view illustrating application of an aqueous scenting composition of the present invention to an air filter of the same general type as the filter shown in FIG. 2 by spraying the composition onto a surface of the filter.

As illustrated in FIG. 3, an aqueous scenting composition 30 of the present invention is applied in spray form 32 directly onto the filter medium 26 from any suitable spray application device 34. In this regard, it should be noted that the spray application device 34 may be a simple button operated spray jar 36 as illustrated herein or may be a more technically advanced pump arrangement such as a Mark IV spray pump system, commercially available from Saint-Gobain Calmar Inc., having a head assembly with interchangeable orifice caps to provide nozzles of varying dimensions for accurate adjustment of the spray droplet size in the spray 32 sprayed onto the surface of the filter medium 26 of the air filters 18 by pumping the spray composition 30 through pre-selected sized orifices formed in the in interchangeable orifice cap.

For example, a head assembly for use in the Mark IV spray pump system to supply a wide spray providing fine sized particle diameters of about 70–75 micron particle diameter employs an orifice cap structured with an 0.020" orifice size, 0.010" land size and 0.008" depth. A head assembly for use in the Mark IV spray pump system to supply a medium spray providing medium sized particle diameters of about 75–80 micron particle diameter employs an orifice cap structured with an 0.013" orifice size, 0.010" land size and 0.010" depth and a head assembly to supply a narrow spray providing large sized particle diameters of about 85–90 micron particle diameter employs an orifice cap structured with an 0.013" orifice size, 0.017" land size and 0.010" depth.

The sprayed on scenting composition 30 adheres to the filter medium 26 of the filter 18 as illustrated in FIGS. 2 and 3, at application points 38 about the surface of the filter medium 26 in the filter 18 and can be applied in essentially any desired or random configuration, shape or form about the surface of the medium 26. In practice, the scenting composition 30 is preferably sprayed onto the filter medium 26 at points 38 around a generally central portion of the filter 18 as shown in FIGS. 2 and 3.

Thus, in accordance with the present invention, spray on, fragranced polymer emulsion compositions are provided for application to scenting devices such as filters used, for example, in central home heating and air conditioning systems. In formulating these polymeric emulsions for use in the present invention, it is necessary to consider that the physical dynamics which transform liquid emulsion polymers into laminated polymer coatings are sensitive to such parameters as chemical composition, particle size, surface tension, drying rates, and a broad range of other such considerations.

In this regard, the formation of a polymer film occurs as the individual polymer particles coalesce. Normally, the polymer particles are held apart by stabilizing forces (i.e., electrostatic and/or steric forces) resulting from the charged polymer chain end groups or surfactants. Transformation of the polymer particles into a clear film requires that these stabilizing forces be exceeded as the continuous water phase becomes evaporated, that the emulsion polymer system be above its minimum film formation temperature (MFFT), that the polymer chosen have the appropriate elastic modulus (resistance to particle deformation) and overall polymer rheology.

Latex polymer emulsions transform into films during the drying process by attractive pressure forces which relate to the surface tension of the continuous water phase and the distance between polymer particles according to the following equation:

Pressure Forces=Surface Tension/Distance Between Polymer Particles.

During application to a scenting device such as an air filter, sprayed emulsion particles become attached to filter fibers (often fiber glass) and quickly form a surface encapsulating film. The surface activity (especially, the wetting forces and contact angle between droplets and fibers) of the spray on emulsion is pre-adjusted to insure that maximum wetting is achieved between the emulsion droplets and filter fibers. This wetting action also helps retard the droplet tendency to collect in larger droplets due to the action of gravity.

Spray droplet size can be regulated by the rheological characteristics of the fragranced polymer emulsion and the orifice characteristics employed in the spray application device such as a spray pump. It should be noted that droplet size is important in regulating the initial and long range perception of air freshening fragrance throughout a household when a scent or fragrance is emitted from an air filter in an HVAC system. Based on studies we have conducted utilizing a Mark IV spray pump head assembly, commercially available from Saint-Gobain Calmar Inc., having interchangeable orifice caps to adjust the droplet size sprayed onto air filters, we have found that spraying of small, fine emulsion particles (e.g., about 70–75 microns in diameter) produced a maximum initial burst of fragrance from a treated filter installed in a standard HVAC system but the fragrance does not last for an extended period of time (about 2–3 days); while spraying larger size emulsion particles (e.g., about 75–85 microns in diameter) on the filter resulted in a longer lasting perception of fragrance (i.e., slower sustained fragrance release) over a longer duration (about 5–8 days); and spraying even larger size emulsion particles (e.g., about 85–90 microns in diameter) resulted in a still longer duration of fragrance perception (about 12–21 days).

With regard to the preparation of the scenting compositions of the present invention, they are formulated in a manner such that they do not create a significant air obstruction and, therefore, do not impede air flow or air heating/cooling efficiencies when sprayed on an air filter in an HVAC system. Furthermore, we have found that if scenting compositions containing fragrance materials only, without any additives, are sprayed onto air filters they may not form a uniform spray pattern of fine droplets and may not be absorbed by or adhere well to the fibers of the filter. As a result, the fragrance materials in the scenting composition will drip and evaporate rapidly.

These formulation problems have been overcome herein by incorporating polymeric emulsifiers into the scenting compositions at levels of from about 1.0 to about 50% by weight of the fragrance mixture. In this manner, the emulsifiers help create a uniform spray pattern of small droplets of fragrance, cause the fragrance adhere to the fibers such as fiberglass fibers of an air filter and act as a fixative to retard the rate of evaporation.

Furthermore, the scenting compositions of this invention are prepared by forming mixtures of fragrance materials (i.e., fragrance oils) in a matrix of polymeric emulsifiers, surfactant film forming agents and water. That is, the fragrance oils are uniformly dispersed throughout the mixture as small droplets as a result of the use of emulsifiers, surfactants, and mechanical mixing. Gums may also be included in the mixture to produce compositions which are similar in appearance and properties to glue and which, when applied to a filter, either by spray or by the drop, adhere to the filter.

The film that forms on the filter is air permeable and, thus, although it retards the rate of evaporation of the fragrance oils, it permits air to pass through the membrane so that the fragrance from the spray can be perceived. In this regard, it should be noted that additives to latex emulsions need to be chosen with great care. Many components will alter the surface charges on the suspended polymer components and cause these particles to prematurely coalesce into a gelatinous phase. Other additives will reduce the continuous phase surface tension and decrease the pressure forces needed for particle/particle lamination into a film.

Air freshening or scenting compositions for use in the present invention may be prepared by a process comprising forming a colloidal dispersion of a latex type emulsion polymer, preferably, a styrene butadiene copolymer, an acrylic polymer, an acrylic urethane hybrid copolymer or a styrene acrylic copolymer in a suitable solvent such as water along with a suitable surfactant and a fragrance material or fragrant component. The surfactant is incorporated in the dispersion to improve clarity, to control the rate of evaporation and/or to aid in the dispersion of the fragrance material blended or dispersed in the solution.

Other emulsion polymers suitable for use in formulating the scenting compositions of the present invention fall into the category of water-borne latex polymers. Such suitable latexes, in addition to styrene butadiene copolymers, acrylic polymers, acrylic urethane hybrid copolymers, and styrene acrylic copolymers, and the like include copolymer blends of predominately vinylidene chloride monomers and ethylenically unsaturated comonomers selected from the group consisting of methyl methacrylates, acrylonitriles and methyl acrylates, and vinylidene chloride-vinyl chloride copolymers and mixtures thereof.

Exemplary of water-borne polyvinylidene chloride-based latex compositions for use herein are the emulsion polymerized vinylidene chloride copolymer latexes such as those sold under the trademark Daran SL112 by W.R. Grace & Co. and those sold by Solvay & Cie under the trademark IXAN WA 50. Another latex for use herein is a uniform colloidal dispersion of vinyl chloride polymers and vinylidene chloride copolymers in water sold by BF Goodrich Company under the trademark Geon 650X18. Each of the foregoing latexes exhibits the necessary film forming properties and contains low concentrations of both anionic and nonionic surfactants. They also have high solids contents (e.g., greater than 50% by weight solids) and demonstrate low, water-like viscosities (e.g. less than 30 cps).

Exemplary of most preferred latex emulsion polymers particularly suitable for use in forming the air freshening or scenting compositions of the present invention are anionically stabilized acrylic-urethane hybrid latex polymers such as Hybridur 570 sold by Air Products and Chemicals Inc.; water based, styrene butadiene latex copolymers such as Tykote 1005 sold by Dow Reichold Speciality Latex; styrene acrylate latex polymers such as Synethemul® 18106 sold by Dow Reichold Speciality Latex LLC; and water based styrene latex polymers such as TyKote® Base sold by Dow Reichold Specialty Latex LLC and the like.

With regard to suitable surfactants for use in the scenting compositions of this invention, we have found that a wide variety of non-ionic and/or cationic surfactants advantageously may be employed in formulating these compositions. Furthermore, the surfactant should have a low odor profile so that it will not interfere with the odor profile of the fragrance. Exemplary of suitable surfactants are nonoxynol-6 sold by Texaco under the tradename Surfonic N60; nonoxynol-9 sold by Rhodia Inc. under the tradename Igepal CO630; Nonoxynol 10 sold by Union Carbide under the tradename Tergitol NP-10; Ceteth 2 sold by Uniqema America under the tradename Bry 72; Steareth-20 sold by Uniqema America under the tradename Bry 78. Nonyl phenols and ethoxylated alcohols are other surfactants that also may be used.

In a preferred embodiment of this invention, the surfactants for use in preparing the aqueous scenting compositions are anionic/nonionic grind aid surfactants for high hydrophilic lipophilic balance (HLB) inorganic pigments such as products having an HLB of 15 which are sold by Air Products & Chemicals Inc. under the tradename Surfonyl CT-131. Other preferred surfactants are ethoxylated alkyl phenols such as a nonionic, octoxynol 9 surfactant product sold by Union Carbide Corp under the trade name Triton X-100 and non-ionic, polysorbate 20 product sold by Uniqema America Inc. under the tradename Tween 20.

A most preferred surfactant for use herein is a solvent free anionic/nonionic grind aid surfactant sold by Air Products & Chemicals, Inc. under the tradename Surfynol CT-171 which has been found to provide both effective pigment wetting and dispersing characteristics as well as latex stabilizing effects in the compositions of the present invention. Other most preferred surfactants for use herein include low foaming, non-ionic surfactants compatible with anionic particles sold by Air Products & Chemicals, Inc. under the tradename Surfynol TG and non-ionic, dimethyl octynediol surfactants sold by Air Products & Chemicals, Inc. under the tradename Surfynol 82.

While many forms of scenting compositions may be used in the present invention; in a preferred embodiment, a scenting composition is provided which releases fragrant material, under typical ambient household conditions, for a predetermined period of time ranging from about one day to several months or more, with a most preferred period being about thirty days.

With regard to fragrance materials suitable for use in the aqueous scenting compositions of the present invention, it should be noted that any desirable known scenting or fragrance materials may be employed to produce such compositions provided that the fragrance is compatible with the aqueous mixture and the formulas are balanced to eliminate partial fractionation. Examples of scents or fragrances for use in producing the aqueous scenting compositions of the present invention include, but are not limited to, Sparkling Citrus scented fragrances such as those sold under the designation F35902 by Flavor & Fragrance Specialties, Inc.; vanilla scented fragrances such as those sold under the designation F33626 by Flavor & Fragrance Specialties, Inc. apple scented fragrances such as those sold under the designation F33628 by Flavor & Fragrance Specialties, Inc.; floral scented fragrance such as those sold under the designation F30482 by Flavor & Fragrance Specialties, Inc. and the like.

Although most fragrances are bactericidal, we have found that in formulating the aqueous scenting compositions of the present invention it should be noted that significant optional ingredients for inclusion in the compositions of the present invention are anti-bacterial or anti-microbial agents which may be included to discourage the growth of microorganisms that may adversely affect the odor or stability of the compositions.

Examples of suitable anti-bacterial or anti-microbial agents for inclusion in the compositions of this invention include chlorhexidine gluconate; propylene glycol, methyl paraben, propyl paraben, imidazolidinyl urea sold under the trade name Abiol by 3V Inc., stabilized chlorine dioxide sold under the trade name Anthlum Dioxcide by International Dioxide, Inc., oxazolidine sold under the trade name Bioban CS-1246 by Angus Chemical Co., substituted triazine sold under the trade name Bioban GK by Angus Chemical Co., oxazolidine blend sold under the trade name Bioban N-95 by Angus Chemical Co., blends of morpholine derivatives sold under the trade name Bioban P-1487 by Angus Chemical Co., silica hydrogel sold under the trade name Britesorb A 100 by The PQ Corp., 5-bromo-5-nitro-1,3 dioxane, 10% solution in propylene glycol sold under the trade name Bronldox-L by Henkel Canada Ltd., 2-bromo-2-nitropropane-1,3 diol sold under the trade name Bronopol by Inolex Chemical Co., DMDM hydantoin sold under the trade name Custom DMDM by Custom Ingredients, Inc., DMDM hydantoin sold under the trade name Dantogard by Lonza Inc., liquid preservative systems sold under the trade name Emercide 1199 by Henkel Canada Ltd., phenoxyethanol sold under the trade name Emeressence 1160 by Henkel Corp. Chemicals Group, blends of morpholine derivatives sold under the trade name Dowicil by Angus Chemical Co., Diazolidinyl urea and parabens sold under the trade name Germaben II-E by Sutton Laboratories, diazolidinyl urea sold under the trade name Germall II by Sutton Laboratories, diazolidinyl urea and iodopropynyl butylcarbamate sold under the trade name Germall Plus by Sutton Laboratories, imidazolidinyl urea sold under the trade name Germall 115 by Sutton Laboratories, iodopropynyl butyl carbamate sold under the trade name Glycacil by Lonza Inc., DMDM hydantoin sold under the trade name Glydant by Lonza Inc., DMDM hydantoin and iodopropynyl butyl carbamate sold under the trade name Glydant Plus by Lonza Inc., DMDM hydantoin and iodopropynyl butyl carbamate sold under the trade name Glydant Plus Liquid by Lonza Inc., hexahydrotriazine sold under the trade name Grotan by Troy Corp., dimethyloldimethylhydantoin sold under the trade name Lanodant DM by R.I.T.A. Corp., propylene glycol (and) DMDM hydantoin (and) methylparaben sold under the trade name Lanoplex 1 by R.I.T.A. Corp., propylene glycol (and) DMDM hydantoin (and) methylparaben (and) propylparaben sold under the trade name Lanoplex 2 by R.I.T.A. Corp., Propylene glycol (and) DMDM hydantoin (and) methyl paraben sold under the trade name Paragon by The McIntyre Group., propylene glycol (and) DMDM hydantoin (and) methyl paraben (and) propyl paraben sold under the trade name Paragon II by The McIntyre Group., phenoxyethanol (and) DMDM hydantoin (and) methyl paraben (and) propyl paraben sold under the trade name Paragon III by The McIntyre Group., Para-chloro-meta-cresol sold under the trade name PCMC by Howard Hall Div. R.W. Greeff and Co., Inc., phenoxyethanol (and) DMDM hydantoin (and) iodopropynylbutyl carbamate sold under the trade name Phenagon PDI by The McIntyre Group., methylparaben sold under the trade name Rita Methylparaben by R.I.T.A. Corp., methylchloroisothiazolinone (and) methylisothiazolinone sold under the trade name Rita Preser 150 by R.I.T.A. Corp., propylparaben sold under the trade name Rita Propylparaben by R.I.T.A. Corp., 2-mercaptopyridine-1-oxide, sodium salt sold under the trade name Sodium Omadine by Olin Corp., cetyl trimethyl ammonium bromide sold under the trade name Bromat by Zeeland Chemicals, Inc., sodium hydroxymethylglycinate sold under the trade name Suttocide A by Sutton Laboratories, Tris(hydroxymethyl)nitromethane sold under the trade name Tris Nitro by Angus Chemical Co., proprietary bactericides sold under the trade name Troysan 142 by Troy Corp., amine adducts sold under the trade name Troysan 174 by Troy Corp., 2(Hydroxymethyl)amino-2-methyl-1-propanol, 78% sold under the trade name Troysan 186 by Troy Corp., amine adducts sold under the trade name Troysan 186-II by Troy Corp., 2-[(Hydroxymethyl)amino]-2-methyl-propanol, 100% sold under the trade name Troysan 192 by Troy Corp., amine adducts sold under the trade name Troysan 192-II by Troy Corp., amine adducts sold under the trade name Troysan 198 by Troy Corp., Tin complexes sold under the trade name Troysan 364 by Troy Corp., Hydantoin sold under the trade name Troysan 395 by Troy Corp., formulations of 1,2 Bendiasothiazolin,3-one (BIT) sold under the trade name Troysan 586 by Troy Corp. and the like.

Other optional additives for inclusion in the compositions of this invention, in addition to the anti-bacterial or anti-microbial agents, include mildewcides which may be included in the formulations, with or without the anti-bacterial/anti-microbial agents, as desired. Exemplary of suitable mildewcidal agents which optionally may be incorporated in the compositions of the present invention include, but are not limited to the following mildewcides: 2-n-octyl-4-isothiazolin-3-one ("Skane M-8"); 3-iodo-2-propanyl butyl carbamate ("Polyphase AF-1""); tetra-chloroisophthalonitril ("Nopcocide N-96"); N-trichloromethyl thiophthalimide ("Fungitrol 11"", "Folpet)"; 2-(thicyanonethylthio) benzothiazole ("Busan"); tributyl tin oxide ("TBTO"); 1,2 benzisothiazolin-3-one, aqueous amine solution ("Proxel")]; butadiene sulfone; butadiene polysulfone; 3,5 dimethyl tetrahydro 1,3,5,2H thiadiazine-2-thione ("Cansan S"); 2,4 dichloro-6-(O-chloroanilino)-s-triazine ("Fugritrol Alpha"); 3,5-dibromo-3'-trifluoromethyl salicanilide ("Flurophene"); 2,3,5,6-tetrachloro-4-(methylsulfonyl) pyridine ("Dow S-13"); diiodomethyl p-tolyl salons ("Amical"); 5,6-dichloro benzoazolinone-2 ("Irgasan FP"); 3,5,3',4 tetrachloro salylanilide ("Irgasan BS-200"); cyclohexylsulfamate ("Onyxide 172"); dinitro-1-methyl heptyl phenyl crotonate ("Karathane"); 2-(4-thiazolyl) benzimidazole ("Metasol TK-100"); p-toluene sulfonamide; sulfur; n-(3-chlorophenyl) itaconmide; tetra methyl thiuram disulfide ("Tuex"); trans 1,2 bis (n-propylsulfonyl) ethylene ("Vancide PA"); n-trichloromethyl tetrahydro phthalimide and zinc.

Further optional additives for inclusion in the compositions of this invention, in addition to the foregoing, are rheological agents for thickening the compositions and for controlling the thixotropic characteristics thereof as well as other rheological properties. Exemplary of the wide variety of suitable rheological agents for use in the present invention are additives such as gums including guar and guar deivatives, clays including montmorillonite, bentonite, vermiculite clays and the like, cellulosics including carboxymethylcellulose, polyanionic cellulosics PAC's) sold by Akzo Nobel under the tradename Gabrosa and the like, dextrins, algins, polymeric thickeners including anionic, hydrophobically modified alkali soluble acrylic emulsions (HASE) sold by Rohm and Haas Company under the trade mark Acusol; thickeners based on polyurethanes sold by Munzing Chemie GmbH under the tradename Tafigel and sold by Sasol Servo B.V. under the tradename Nuvis and like rheological agents, and mixtures thereof.

The following examples are intended for illustration purposes only, and should not be deemed to limit the scope of the invention as defined in the appended claims.

EXAMPLE 1

An aqueous scenting composition in accordance with the present invention having a Sparkling Citrus scent was formulated in the laboratory by mixing the following ingredients:

| Wt. % | Ingredients |
| --- | --- |
| 30.00 | Latex Polymer Emulsion (Hybridur 570*) |
| 0.50 | Surfactant (Surfynol CT-171**) |
| 29.50 | Water |
| 40.00 | Sparkling Citrus Fragrance Material (FFS Fragrance F35902***) |

*Hybridur 570 is one of a series of anionically stabilized acrylic-urethane hybrid latex polymers sold by Air Products and Chemicals Inc.
**Surfynol CT-171 is a solvent free anionic/nonionic grind aid surfactant which provides both effective pigment wetting and dispersing characteristics as well as latex stabilizing effects sold by Air Products Inc.
***FFS Fragrance F35902 is a Sparkling Citrus fragrance sold by Flavor & Fragrance Specialties, Inc.

In preparing this composition, the water content of the composition was initially introduced into a main batching vessel at ambient temperature. Then, the latex polymer emulsion was added to the water with moderate stirring. Thereafter, the surfactant and then the fragrance were added with continued mixing until a suitable aqueous spray composition was produced.

The resulting aqueous composition containing the acrylic-urethane hybrid latex polymer emulsion was sprayed onto fiberglass filters and was found to spray well without droplet coalescence and running. After the dried spray on filters were installed in a standard home HVAC system, full home air freshness/scent was detected for more than 15 days.

EXAMPLE 2

An aqueous scenting composition in accordance with the present invention having a vanilla scent was formulated in the laboratory by mixing the following ingredients:

| Wt. % | Ingredients |
| --- | --- |
| 40.00 | Latex Polymer Emulsion (Tykote 1005*) |
| 0.50 | Surfactant (Surfynol CT-131**) |
| 29.50 | Water |
| 30.00 | Fragrance Material (FFS Fragrance F33626***) |

*Tykote 1005 is a water based, styrene butadiene latex copolymer sold by Dow Reichold Speciality Latex.
**Surfonyl CT-131 is an anionic/nonionic grind aid surfactant for high HLB 15 inorganic pigments sold by Air Products & Chemicals Inc.
***FFS Fragrance F33626 is a vanilla scented fragrance sold by Flavor & Fragrance Specialties, Inc.

In accordance with the procedure described in Example 1, this composition was prepared by introducing the water content of the composition into a main batching vessel at ambient temperature. Then, the latex polymer emulsion was added to the water with moderate stirring. Thereafter, the surfactant and then the fragrance were added with continued mixing until a suitable aqueous spray composition was produced.

The resulting aqueous composition containing the styrene butadiene latex polymer emulsion was found to produce excellent grab onto furnace filter fibers and to provide long lasting fragrance release characteristics when the filters were installed in standard home HVAC systems.

EXAMPLE 3

An aqueous scenting composition in accordance with the present invention having an apple scent was formulated in the laboratory by mixing the following ingredients:

| Wt. % | Ingredients |
| --- | --- |
| 35.00 | Latex Polymer Emulsion (Synthemul® 18106*) |
| 0.50 | Surfactant (Triton X100**) |
| 0.50 | Surfactant (Surfynol TG***) |
| 24.00 | Water |
| 40.00 | Fragrance Material (FFS Fragrance F33628****) |

*Synethemul® 18106 is a styrene acrylate latex polymer sold by Dow Reichold Speciality Latex LLC
**Triton X100 is a nonionic, Octoxynol 9, surfactant from Union Carbide Corp.
***Surfynol TG is a low foaming, non-ionic surfactant that is compatible with anionic particles sold by Air Products Inc.
****FFS Fragrance F33628 is an apple scented fragrance sold by Flavor & Fragrance Specialties, Inc.

This composition was prepared by introducing the water content of the composition into a main batching vessel at ambient temperature. Then, the latex polymer emulsion was added to the water with moderate stirring. Thereafter, the mixture of surfactants was added followed by the fragrance with continued mixing until a suitable aqueous spray composition was produced.

The resulting aqueous composition containing a styrene acrylate latex polymer emulsion along with a mixture of surfactants was found to produce excellent spray on characteristics with long lasting apple scented fragrance release properties when applied onto a furnace filter installed in standard home HVAC system.

EXAMPLE 4

An aqueous scenting composition in accordance with the present invention having a floral scent was formulated in the laboratory by mixing the following ingredients:

| Wt. % | Ingredients |
| --- | --- |
| 40.00 | Latex Polymer Emulsion (TyKote® Base*) |
| 0.50 | Surfactant (Tween 20**) |
| 0.50 | Surfactant (Surfynol 82***) |
| 0.10 | Antimicrobial Agent (Kathon CG/ICP***) |
| 23.90 | Water |
| 35.00 | Fragrance Material (FFS Fragrance F30482*****) |

*TyKote® Base is a clear, water based styrene latex polymer sold by Dow Reichold Specialty Latex LLC
**Tween 20 is a non-ionic, polysorbate 20, sold by Uniqema America Inc.
***Surfynol 82 is a non-ionic, dimethyl octynediol surfactant sold by Air Products & Chemicals.
****KathonCG/JCP is an antimicrobial blend of 5-chloro-2-methyl-4-isothiazolin03-one and 2-methyl-4 isothiazolin-3-one, sold by Rohm and Haas.
*****FFS Fragrance F30482 is a floral scented fragrance sold by Flavor & Fragrance Specialties, Inc.

This composition was prepared by introducing the water content of the composition into a main batching vessel at ambient temperature. Then, the latex polymer emulsion was added to the water with moderate stirring. Thereafter, the mixture of surfactants was added followed by the antimicrobial blend of additives and, then, the fragrance was added, with continued mixing, until a suitable aqueous spray composition was produced.

The resulting aqueous composition containing the water based styrene latex polymer emulsion along with a mixture of surfactants and the antimicrobial blend of additives was found to produce a clear barrier film when sprayed on an air filter in a standard home HVAC system and the filter having the composition applied thereon demonstrated excellent fragrance release characteristics and dust resistance and antimicrobial protection over an extended period of time.

EXAMPLE 5

An aqueous scenting composition in accordance with the present invention having a country berry scent was formulated in the laboratory by mixing the following ingredients:

| Wt. % | Ingredients |
|---|---|
| 40.00 | Latex Polymer Emulsion (Hybridur 570*) |
| 0.50 | Surfactant (Surfynol CT-131**) |
| 1.00 | Rheological Agent (Acusol 880***) |
| 28.50 | Water |
| 30.00 | Fragrance Material (FFS Fragrance F35903****) |

*Hybridur 570 is one of a series of anionically stabilized acrylic-urethane hybrid latex polymers sold by Air Products and Chemicals Inc.
**Surfonyl CT-131 is an anionic/nonionic grind aid surfactant for high HLB 15 inorganic pigments sold by Air Products & Chemicals Inc.
***Acusol 880 is a nonionic acrylic liquid thickener sold by Rohm and Haas.
****FFS Fragrance F35903 is a country berries scented fragrance sold by Flavor & Fragrance Specialties, Inc.

This composition was prepared by introducing the water content of the composition into a main batching vessel at ambient temperature. Then, the rheological agent was added to the water with moderate stirring followed by the addition of the latex polymer emulsion in the vessel. Thereafter, the surfactant was added followed by the fragrance, with continued mixing, until a suitable aqueous spray composition was produced.

The resulting aqueous composition containing a mixture of the non-ionic/anionic surfactant and the rheological agent was found to spray well without droplet coalescence and running when sprayed on an air filter in a standard home HVAC system and the filter having the composition applied thereon demonstrated excellent fragrance release characteristics over an extended period of time.

While the present invention has been described in connection with a preferred embodiment, it will be apparent to those skilled in the art that many changes and modifications may be made without departing from the true spirit and scope of the invention. Accordingly, it is intended by the appended claims to cover all such changes and modifications as come within the spirit and scope of the invention.

What is claimed is:

1. An aqueous scenting composition formulated for spray application on an air scenting device for use in an HVAC system to form an air permeable barrier film which slows the rate of water evaporation and provides long lasting freshening or scenting of air flowing through the device with minimal blockage of air flow through the device consisting essentially of:

(a) a latex polymer emulsion selected from the group consisting of styrene butadiene copolymers, acrylic polymers, acrylic urethane hybrid copolymers, styrene acrylic copolymers and mixtures thereof in an amount of between about 10% and about 50% by weight of the composition with the mean particle size of the polymers/copolymers in the emulsion being between about 75 and about 90 microns in diameter;

(b) a surfactant selected from the group consisting of non-ionic and anionic surfactants and mixtures thereof;

(c) a fragrance material in an amount of between about 20% and about 40% by weight of the composition; and wherein the polymer emulsion includes a solids content of latex polymer and fragrance material greater than about 50% by weight of the composition.

2. The aqueous scenting composition of claim 1 wherein the latex polymer emulsion is a water-borne latex polymer.

3. The aqueous scenting composition of claim 1 wherein the surfactant is a solvent free anionic/nonionic grind aid surfactant.

4. The aqueous scenting composition of claim 1 wherein the surfactant is selected from the group consisting of low foaming, non-ionic surfactants compatible with anionic particles, non-ionic, dimethyl octynediol surfactants, ethoxylated alkyl phenols, non-ionic, octoxynol 9 surfactants, non-ionic, polysorbate 20 and mixtures thereof.

5. The aqueous scenting composition of claim 1 including a rheological agent.

6. The aqueous scenting composition of claim 5 wherein the rheological agent is selected from the group consisting of gums, clays and cellulosics, dextrins, algins, polymeric thickeners and mixtures thereof.

7. The aqueous scenting composition of claim 1 including an antimicrobial agent.

8. An aqueous scenting composition formulated for spray application on an air scenting device for use in an HVAC system to provide long lasting freshening or scenting of air flowing though the device with minimal blockage of air flow through the device consisting essentially of:

(a) a latex polymer emulsion selected from the group consisting of styrene butadiene copolymers, acrylic polymers, acrylic urethane hybrid copolymers, styrene acrylic copolymers and mixtures thereof in an amount of between about 10% and about 50% by weight of the composition with the mean particle size of the polymers/copolymers in the emulsion being between about 75 and about 90 microns in diameter;

(b) a surfactant selected from the group consisting of non-ionic and anionic surfactants and mixtures thereof, (c) a fragrance material in an amount of between about 20% and about 40% by weight of the composition; and wherein the polymer emulsion includes a solids content of latex polymer and fragrance material greater than about 50% by weight of the composition.

9. The aqueous scenting composition of claim 8 including a rheological agent.

10. The aqueous scenting composition of claim 8 including an antimicrobial agent.

* * * * *